US008644928B2

(12) United States Patent
Takata

(10) Patent No.: US 8,644,928 B2
(45) Date of Patent: Feb. 4, 2014

(54) NERVE STIMULATION DEVICE

(75) Inventor: Yuhei Takata, Tokyo (JP)

(73) Assignee: Olympus Corporation, Tokyo (JP)

(*) Notice: Subject to any disclaimer, the term of this patent is extended or adjusted under 35 U.S.C. 154(b) by 462 days.

(21) Appl. No.: 12/881,336

(22) Filed: Sep. 14, 2010

(65) Prior Publication Data
US 2011/0093029 A1  Apr. 21, 2011

(30) Foreign Application Priority Data
Oct. 15, 2009  (JP) ................ 2009-238229

(51) Int. Cl.
*A61N 1/00* (2006.01)
(52) U.S. Cl.
USPC ............................................. 607/14
(58) Field of Classification Search
USPC ............................. 607/14, 17; 600/509
See application file for complete search history.

(56) References Cited

U.S. PATENT DOCUMENTS

| 7,512,439 B1 * | 3/2009 | Farazi | 600/509 |
| 2003/0065365 A1 | 4/2003 | Zhu et al. | |

FOREIGN PATENT DOCUMENTS

| JP | 8-509893 A | 10/1996 |
| JP | 2004-173790 | 6/2004 |
| JP | 2004-351122 A | 12/2004 |
| JP | 2008-296014 A | 12/2008 |
| JP | 2010-512833 A | 4/2010 |
| WO | 95/08367 A1 | 3/1995 |
| WO | 2008/073235 A1 | 6/2008 |
| WO | 2008/143814 A2 | 11/2008 |
| WO | 2009/035515 A1 | 3/2009 |

* cited by examiner

*Primary Examiner* — Christopher D Koharski
*Assistant Examiner* — Nadia Ahmad
(74) *Attorney, Agent, or Firm* — Scully, Scott, Murphy & Presser, P.C.

(57) ABSTRACT

To shorten the length of a lead, alleviate physical burden on a patient in installation of a device into a body, and miniaturize the device while allowing both treatment based on cardiac stimulation and nerve stimulation. Provided is a nerve stimulation device implanted in the body together with a cardiac treatment device supplying an electric pulse to a heart depending on a cardiac rate, including a stimulation signal outputting part that stimulates a vagus nerve via a stimulation electrode disposed on the vagus nerve, an electric signal detecting part that detects an electric signal transmitted through a tissue outside the heart by a detection electrode disposed on the tissue, a cardiac event determining part that determines a cardiac event containing the electric pulse supplied to the heart by the cardiac treatment device based on the electric signal detected by the electric signal detecting part, and a controlling part that controls the stimulation signal outputting part based on the cardiac event determined by the cardiac event determining part.

10 Claims, 7 Drawing Sheets

NERVE STIMULATION DEVICE

BACKGROUND OF THE INVENTION

1. Field of the Invention

The present invention relates to a nerve stimulation device.

This application is based on Japanese Patent Application No. 2009-238229, the content of which is incorporated herein by reference.

2. Description of Related Art

Conventionally, cardiac treatment devices that cure arrhythmia by stimulating a heart or a vagus nerve depending on a cardiac rate are known (see, for example, Japanese Unexamined Patent Application, Publication No. 2004-173790).

However, in the case of the cardiac treatment device of Japanese Unexamined Patent Application, Publication No. 2004-173790, since a lead extending from the device main body is disposed on each of the heart and the vagus nerve that are located in distant positions, a long lead is required. Such a long lead may affect a tissue located in the course of the lead, or cause a noise on an electric signal transmitted through the lead, or increased electric power consumption.

When a treatment by nerve stimulation is required for a patient who has already had a defibrillator or a pacemaker implanted therein, it is necessary to remove such a device from the body and to newly install a cardiac treatment device. This is problematic in that physical burden on the patient is large. The cardiac treatment device has both arrangements for cardiac stimulation and nerve stimulation, it is necessary to have an arrangement for electrically insulating or separating electric signals of cardiac stimulation and nerve stimulation for preventing these electric signals from interfering each other, so that the dimension of the device increases.

BRIEF SUMMARY OF THE INVENTION

The present invention provides a nerve stimulation device that is implanted in a body together with a cardiac treatment device for supplying an electric pulse to a heart depending on a cardiac rate, including a stimulation signal outputting part that stimulates the vagus nerve via a stimulation electrode disposed on the vagus nerve, an electric signal detecting part that detects an electric signal transmitted through a tissue outside the heart by a detection electrode disposed on the tissue, a cardiac event determining part that determines a cardiac event containing the electric pulse supplied to the heart by the cardiac treatment device based on the electric signal detected by the electric signal detecting part, and a controlling part that controls the stimulation signal outputting part based on the cardiac event determined by the cardiac event determining part.

According to the present invention, by stimulation on the vagus nerve by the stimulation signal outputting part, it is possible to cure the arrhythmia by lowering the cardiac rate to a normal range.

In this case, when the electric pulse is supplied to the heart by the cardiac treatment device, the electric pulse is transmitted to the detection electrode through the tissue outside the heart, so that the electric signal detected by the electric signal detecting part changes. The cardiac event determining part determines the cardiac event containing supply of the electric pulse by the cardiac treatment device based on the change in electric signal detected by the electric signal detecting part, and the controlling part controls stimulation on the vagus nerve by the stimulation signal outputting part based on the determination result.

That is, a treatment by nerve stimulation in cooperation with the operation of the cardiac treatment device can be realized even with the configuration that is electrically separated from the cardiac treatment device. Since the device can be installed into the patient already having the cardiac treatment device implanted therein at a different timing in a different position from the cardiac treatment device, it is possible to alleviate the physical burden on the patient by installing the nerve stimulation device without removing the cardiac treatment device. Since there is no need to provide an arrangement for electrically insulating from the cardiac treatment device, it is possible to miniaturize the device by simplifying the configuration. Since both the stimulation electrode and the detection electrode are installed outside the heart, it is possible to shorten the lead that connects these electrodes and the device main body by appropriately selecting the arrangement.

In the present invention as described above, a filtering part that removes a noise from the electric signal detected by the electric signal detecting part may be provided.

In this way, it is possible to improve the detection accuracy of an intended electric signal.

In the present invention as described above, the cardiac event determining part may determine that the electric pulse is a shock pulse for defibrillation when the voltage of the electric signal detected by the electric signal detecting part is more than or equal to a predetermined threshold.

In this manner, it is possible to easily distinguish the shock pulse from other cardiac events.

In the present invention as described above, the controlling part may attenuate the stimulation on the vagus nerve by the stimulation signal outputting part or may enhance the stimulation on the vagus nerve by the stimulation signal outputting part when the cardiac event determining part determines that the electric pulse is the shock pulse.

In this manner, it is possible to alleviate the burden on the heart after supply of the shock pulse in accordance with the condition of the heart of the individual patient, or to improve the curing effect of arrhythmia and realize more appropriate treatment of the heart.

In the present invention as described above, the cardiac event determining part may determine that the electric pulse is a pacing pulse for pacing a cardiac beat, when the voltage of the electric signal detected by the electric signal detecting part is more than or equal to a first predetermined threshold and smaller than a second predetermined threshold that is larger than the first predetermined threshold.

In this manner, it is possible to easily distinguish the pacing pulse from other cardiac events.

In the present invention as described above, the cardiac event determining part may determine that the pacing pulse is an antitachycardia pacing pulse when it sequentially determines that the electric pulse is the pacing pulse in a time interval shorter than a predetermined time, and the number of sequential determinations of the pacing pulse is more than or equal to a predetermined threshold.

In this manner, it is possible to determine the condition of the heart more accurately.

In the present invention as described above, the controlling part may enhance the stimulation on the vagus nerve by the stimulation signal outputting part when the cardiac event determining part determines that the electric pulse is the antitachycardia pacing pulse.

In this manner, it is possible to cure the tachycardia more effectively.

In the present invention as described above, the cardiac event determining part may determine that the pacing pulse is a bradycardia pacing pulse when it sequentially determines that the electric pulse is the pacing pulse in a time interval shorter than a predetermined time, and the number of sequential determinations of the pacing pulse is smaller than a predetermined threshold.

In the present invention as described above, the controlling part may attenuate the stimulation on the vagus nerve by the stimulation signal outputting part when the cardiac event determining part determines that the electric pulse is the bradycardia pacing pulse.

In this manner, it is possible to cure the bradycardia more effectively.

According to the present invention, advantageously it is possible to shorten the length of the lead, and to alleviate physical burden on a patient in insertion of the device into the body, and miniaturize the device while allowing both treatment based on cardiac stimulation and nerve stimulation.

DETAILED DESCRIPTION OF THE INVENTION

A nerve stimulation device 1 according to one embodiment of the present invention will be described below with reference to the drawings.

Figure 1:
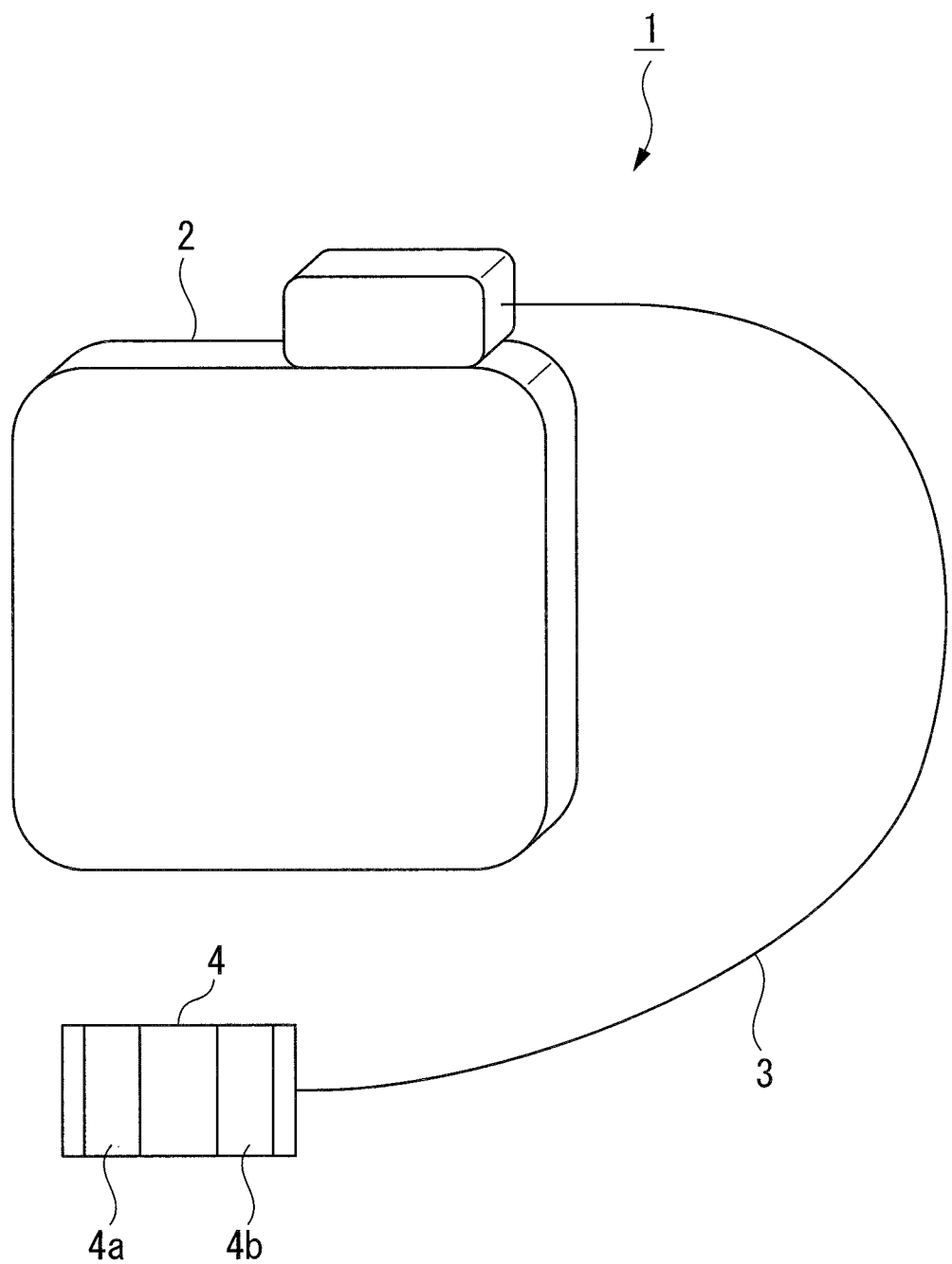
FIG. 1 is an overall configuration view of a nerve stimulation device according to one embodiment of the present invention.
Figure 2:
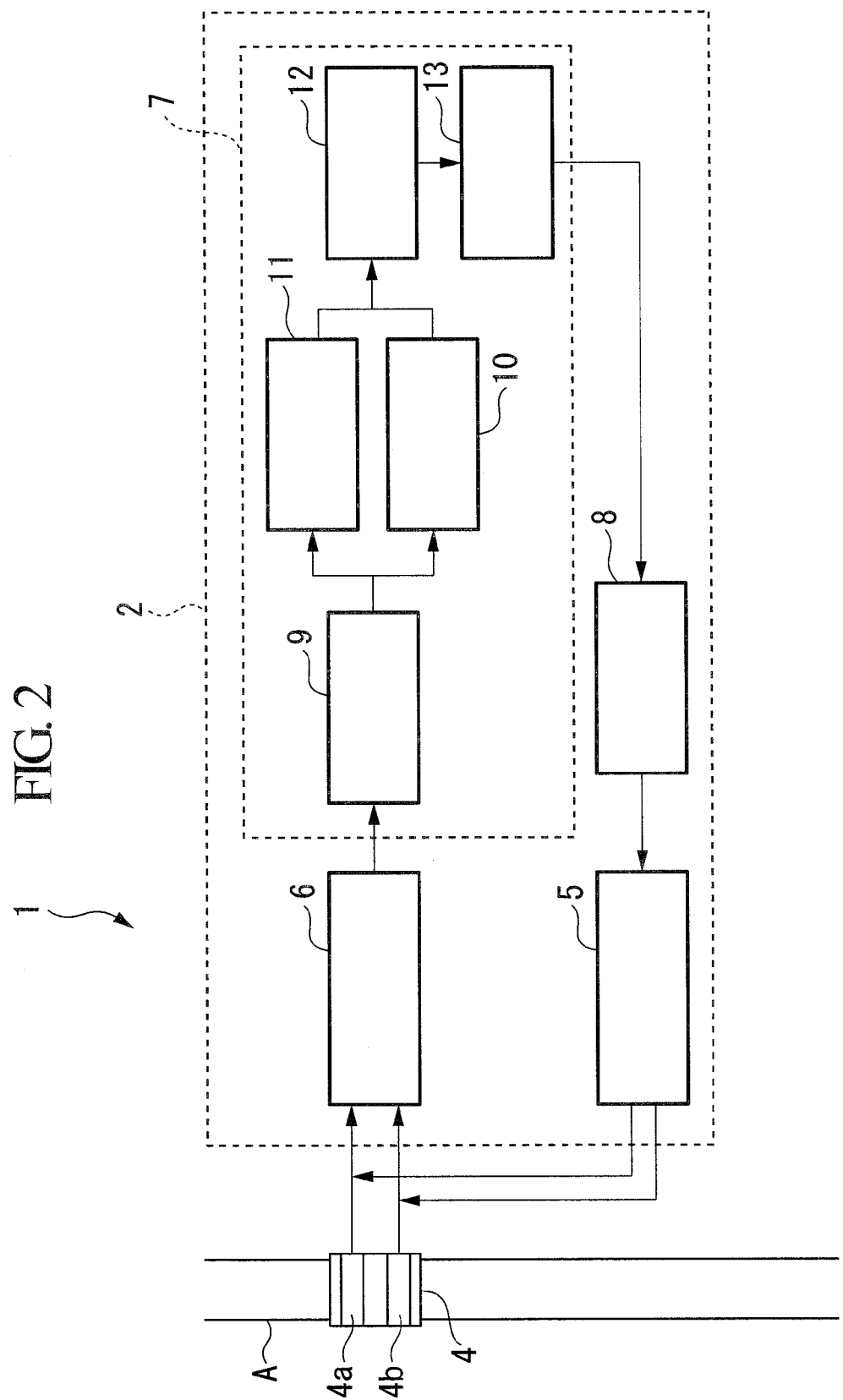
FIG. 2 is a block diagram showing functions of the nerve stimulation device in FIG. 1.

As shown in FIG. 1, the nerve stimulation device 1 according to the present embodiment has a device main body 2 to be implanted into a body, and an electrode part (stimulation electrode, detection electrode) 4 connected to the device main body 2 via a lead 3. As shown in FIG. 2, the device main body 2 has a stimulation signal outputting part 5 for outputting a stimulation pulse to the electrode part 4, an electric signal detecting part 6 for detecting voltage change of the electrode part 4, a cardiac event determining part 7 for determining a cardiac event occurring in a heart B, and a controlling part 8 for controlling output of a stimulation pulse by the stimulation signal outputting part 5.

The electrode part 4 has an anode electrode 4a and a cathode electrode 4b that are electrically insulated from each other. The electrode part 4 is formed into a cylindrical shape, for example, so that it is attached to cover the lateral face of a vagus nerve A circumferentially.

The stimulation signal outputting part 5 generates a stimulation pulse, and outputs the stimulation pulse between the electrodes 4a and 4b via the lead 3. As a result, the vagus nerve A in the position between the electrodes 4a and 4b is stimulated by the stimulation pulse and excited, so that the cardiac rate decreases. The stimulation signal outputting part 5 increases or decreases energy of the stimulation pulse by lengthening or shortening the pulse width of the stimulation pulse generated by the same, and thus enhances or attenuates the stimulation given to the vagus nerve A.

The electric signal detecting part 6 detects an electric signal transmitted through the vagus nerve A or a tissue near the vagus nerve A by detecting the voltage across the electrodes 4a and 4b.

The cardiac event determining part 7 includes a pulse detection circuit 9 that detects a pulse waveform appearing in the electric signal detected by the electric signal detecting part 6, a current detection circuit 10 that detects a current value flowing between the electrodes 4a and 4b, a voltage detection circuit 11 that detects a voltage value across the electrodes 4a and 4b, a pulse number counting circuit 12 that counts the number of times a pulse waveform is detected by the electric signal detecting part 6, and a determination circuit 13 that determines a kind of cardiac event based on the values detected or counted in the circuits 9 to 12.

The pulse detection circuit 9 stores a voltage value of an electric signal detected by the electric signal detecting part 6, and detects a pulse waveform when a change rate of voltage value is greater than a predetermined threshold, namely when a rising part of a pulse waveform appears in the electric signal.

The current detection circuit 10 detects a current value between the electrodes 4a and 4b when the pulse waveform is detected by the pulse detection circuit 9.

The voltage detection circuit 11 detects a voltage value across the electrodes 4a and 4b when the pulse waveform is detected by the pulse detection circuit 9.

The pulse number counting circuit 12 counts the number of times the pulse detection circuit 9 sequentially detects the pulse waveform in a time interval shorter than a predetermined time, when the current value detected by the current detection circuit 10 is smaller than a predetermined threshold and the voltage value detected by the voltage detection circuit 11 is more than or equal to a predetermined threshold. Here, the term "predetermined time" refers to approximately a time interval of cardiac beat in a normal condition.

The determination circuit 13 determines that the pulse waveform results from a shock pulse supplied to the heart B, when the current value detected by the current detection circuit 10 is more than or equal to a predetermined threshold. The determination circuit 13 determines that the pulse waveform results from a spontaneous cardiac beat of the heart B when the current value detected by the current detection circuit 10 is smaller than a predetermined threshold and the voltage value detected by the voltage detection circuit 11 is smaller than a predetermined threshold.

The determination circuit 13 determines that the pulse waveform results from a pacing pulse supplied to the heart B, when the current value detected by the current detection circuit 10 is smaller than a predetermined threshold and the voltage value detected by the voltage detection circuit 11 is more than or equal to a predetermined threshold. At this time, the determination circuit 13 determines that the pacing pulse is a bradycardia pacing pulse when the number of times the pulse waveform is detected by the pulse detection circuit 9, counted by the pulse number counting circuit 12 is more than or equal to a predetermined threshold, and determines that the pacing pulse is an antitachycardia pacing pulse when it is smaller than the predetermined threshold.

The controlling part 8 makes the stimulation signal outputting part 5 supply the vagus nerve A with a stimulation pulse, for example, intermittently on a constant time cycle. The controlling part 8 disrupts the nerve stimulation by the stimulation signal outputting part 5 for a certain period of time when the determination circuit 13 determines that the pulse waveform resulting from the shock pulse is detected. The controlling part 8 disrupts or attenuates the nerve stimulation by the stimulation signal outputting part 5 for a certain period of time when the determination circuit 13 determines that the pulse waveform resulting from the bradycardia pacing pulse is detected. The controlling part 8 enhances the nerve stimulation by the stimulation signal outputting part 5 when the determination circuit 13 determines that the pulse waveform resulting from the antitachycardia pacing pulse is detected.

An operation of the nerve stimulation device 1 configured as described above will be described below.

Figure 3:
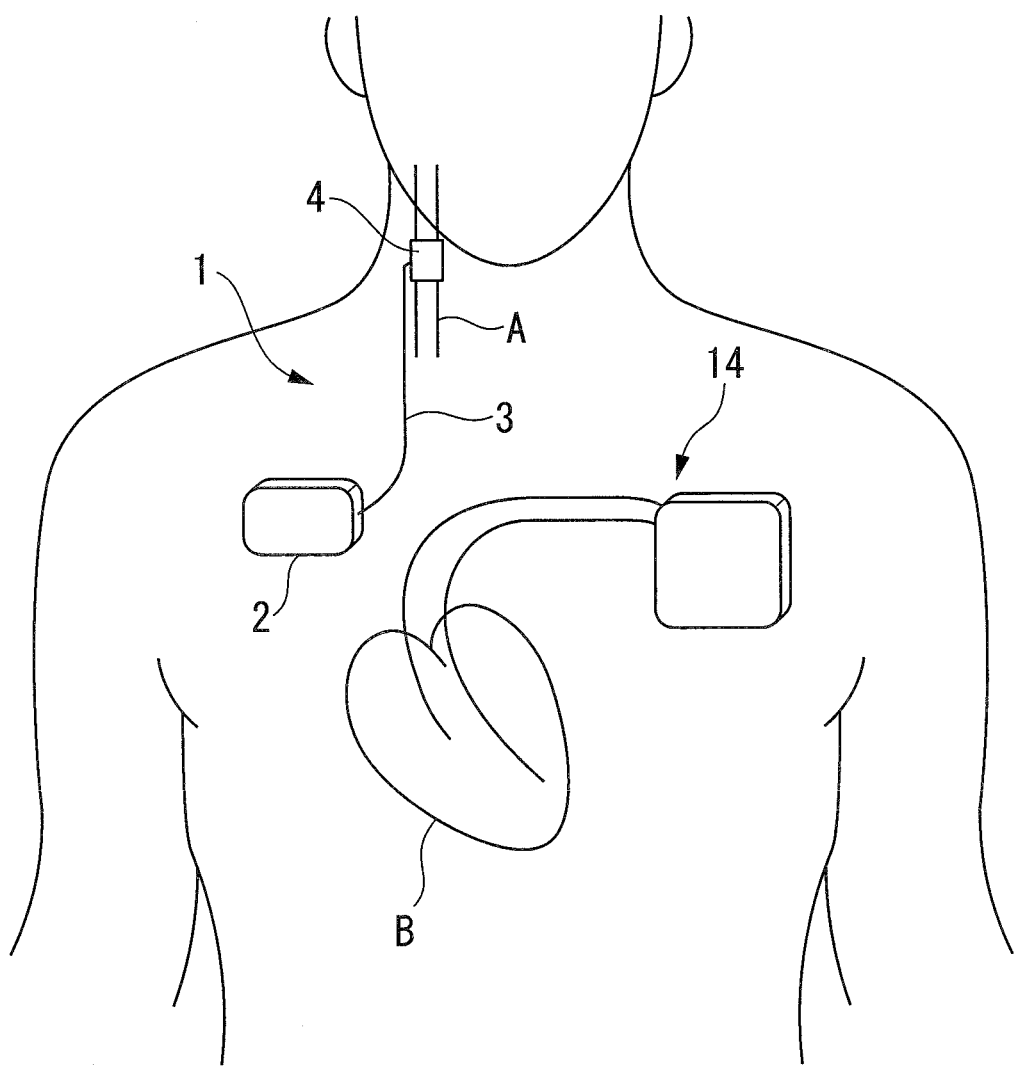
FIG. 3 is a view showing an example of installation of the nerve stimulation device in FIG. 1 into a body.

The nerve stimulation device 1 according to the present embodiment is implanted into a site different from that of the cardiac treatment device 14, in a patient already having the cardiac treatment device 14 implanted in a body, and the electrode part 4 is disposed on the vagus nerve A. In the example shown in FIG. 3, the cardiac treatment device 14 is implanted near the left clavicle, the nerve stimulation device 1 is implanted near the right clavicle, and the electrode part 4 is disposed on the vagus nerve A of the cervical region. Upon start of the operation, the nerve stimulation device 1 detects an electric signal near the vagus nerve A and stimulates the vagus nerve A intermittently.

When fibrillation occurs in the heart B and a shock pulse is supplied to the heart B by the cardiac treatment device 14, the nerve stimulation device 1 disrupts the nerve stimulation for a certain period of time and waits for recovery of the hemodynamics of the heart B, and then resumes the nerve stimulation. When tachycardia occurs in the heart B, and an antitachycardia pacing pulse that is successive in a relatively short time interval is supplied by the cardiac treatment device 14, the nerve stimulation device 1 suppresses the increase in cardiac rate more strongly by continuing the nerve stimulation with enhanced intensity. When bradycardia occurs in the heart B, and a bradycardia pacing pulse is supplied to the heart B once or several times by the cardiac treatment device 14, the nerve stimulation device 1 disrupts the nerve stimulation for a certain period or time and then resumes the same, or continues the nerve stimulation with reduced intensity to prevent excess drop in cardiac rate.

As described above, according to the present embodiment, the nerve stimulation device 1 operates in cooperation with the operation of the cardiac treatment device 14, although it is electrically separated from the cardiac treatment device 14. This provides the merit that treatment of the heart B based on the cardiac stimulation and the nerve stimulation can be appropriately conducted even for the patient already having the cardiac treatment device 14 implanted in the body, by newly installing only the nerve stimulation device 1 while leaving the cardiac treatment device 14 in the body. Since there is no need to remove the cardiac treatment device 14 at this time, such a merit arises that physical burden on the patient can be alleviated, and the surgery can be simplified.

As described above, since the device is electrically separated from the cardiac treatment device 14, the electric signal transmitted through the lead 3 or the device main body 2 will not interfere with an electric signal of the cardiac stimulation. Therefore, it is possible to eliminate the need of the arrangement such as an insulating means and simplify the configuration, and to miniaturize the device main body 2. Since the disposition of the nerve stimulation device 1 is not restricted by the cardiac treatment device 14, it is possible to make the length of the lead 3 relatively short by placing the electrode part 4 and the device main body 2 so that they are close to each other. As a result, it is possible to reduce the influence of the lead 3 or the electric signal transmitted through the lead 3 on tissues in the body, and to reduce the electric power consumption by detecting the electric signal more accurately by reducing the noise contained in the electric signal during transmission through the lead 3.

Figure 4:
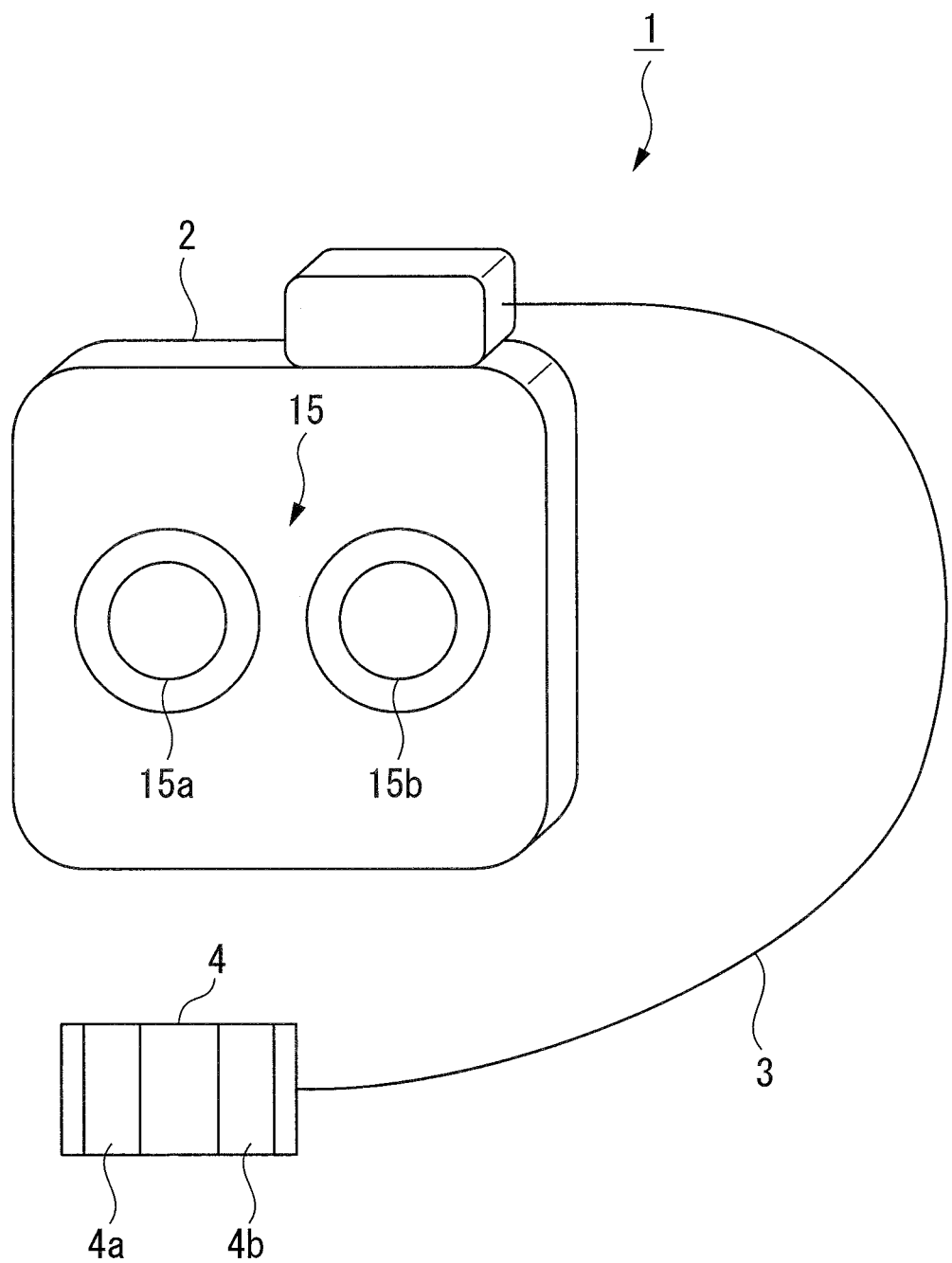
FIG. 4 is a view showing a modified example of the nerve stimulation device in FIG. 1, and showing a configuration when the device main body is provided with another electrode part.

While the electric signal transmitted from the heart B is detected by the electrode part 4 disposed on the vagus nerve A in the above embodiment, alternatively, it may be detected by another electrode part (detection electrode) 15 provided in the device main body 2 as shown in FIG. 4.

Also as another electrode part 15, a bipolar electrode having an anode electrode 15a and a cathode electrode 15b is used. Also in this way, it is possible to detect the pulse waveforms resulting from the spontaneous cardiac beat, the shock pulse, and the pacing pulse transmitted from the heart B, from change in voltage across the electrodes 15a and 15b.

Figure 5:
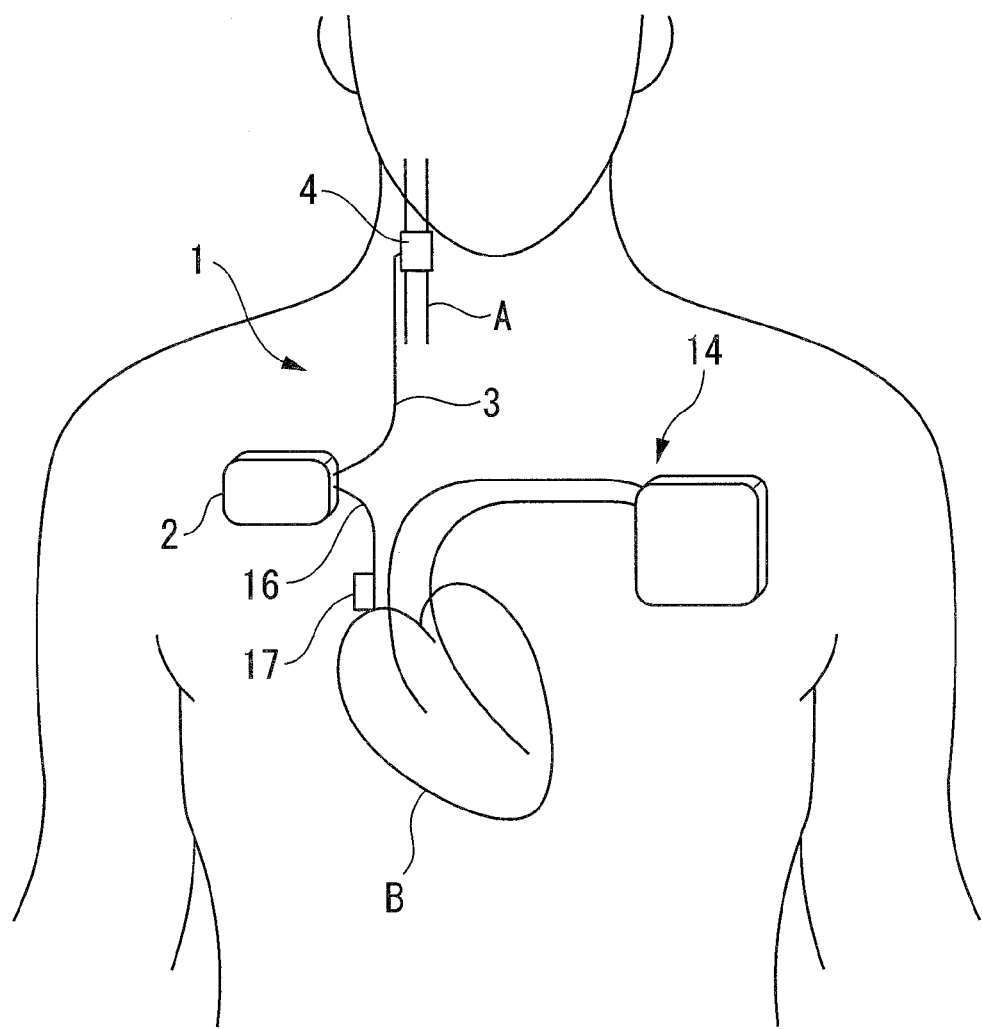
FIG. 5 is a view showing another modified example of the nerve stimulation device in FIG. 1, and showing an example of installation of the device into a body when another lead and electrode part are provided.

In the above embodiment, another electrode part (detection electrode) 17 that is connected to the device main body 2 via another lead 16 may be provided as shown in FIG. 5, and the electrode part 17 may be disposed near the heart B.

In this manner, it is possible to detect the pulse waveform resulting from the cardiac event more accurately while shortening the lead 3 connected to the vagus nerve A.

Figure 6:
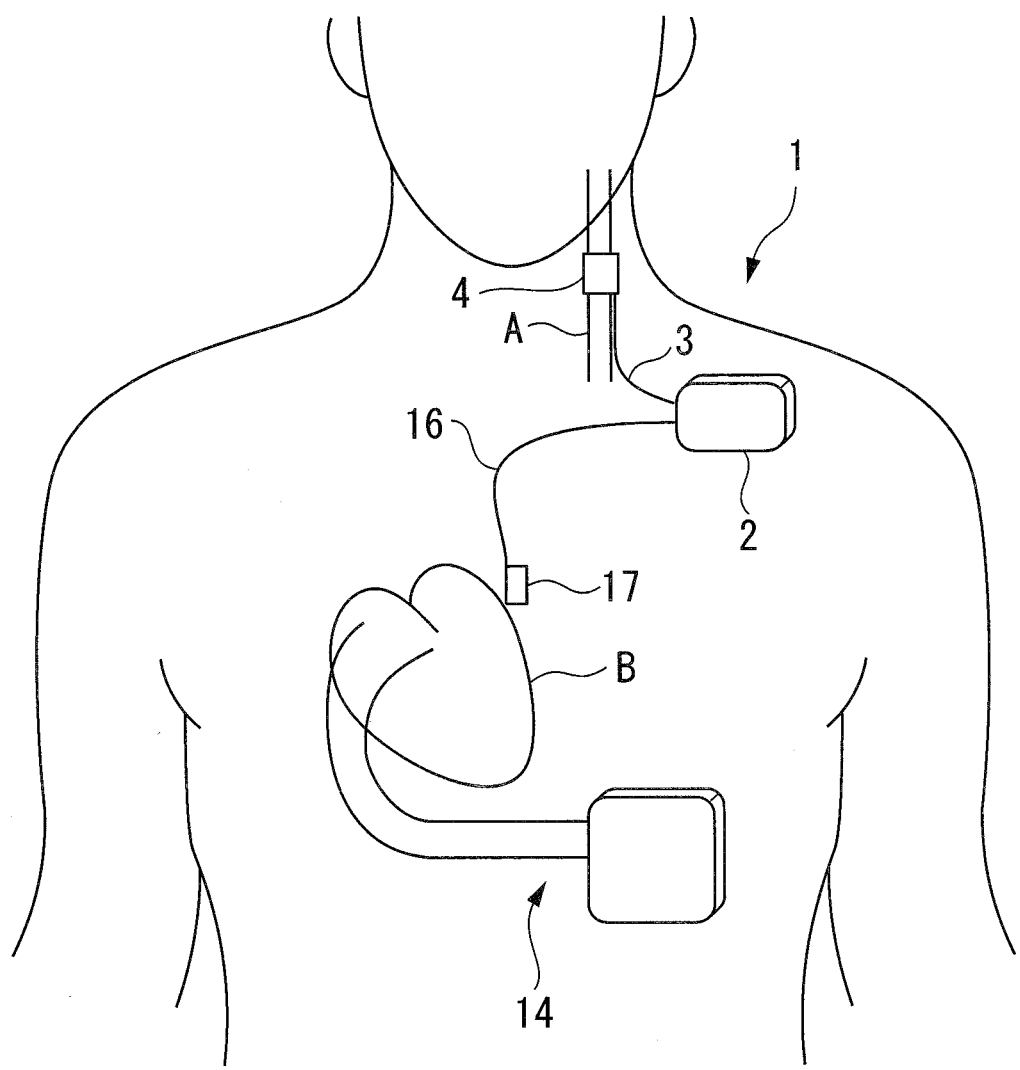
FIG. 6 is a view showing another example of installation of the nerve stimulation device in FIG. 1 into a body.

In the above embodiment, disposition of the device main body 2 is not particularly limited, and may be appropriately selected depending on disposition of the cardiac treatment device 14. For example, as shown in FIG. 6, when the cardiac treatment device 14 is disposed below the heart B, the device main body 2 may be disposed near the clavicle on the same side with the cardiac treatment device 14.

Figure 7:
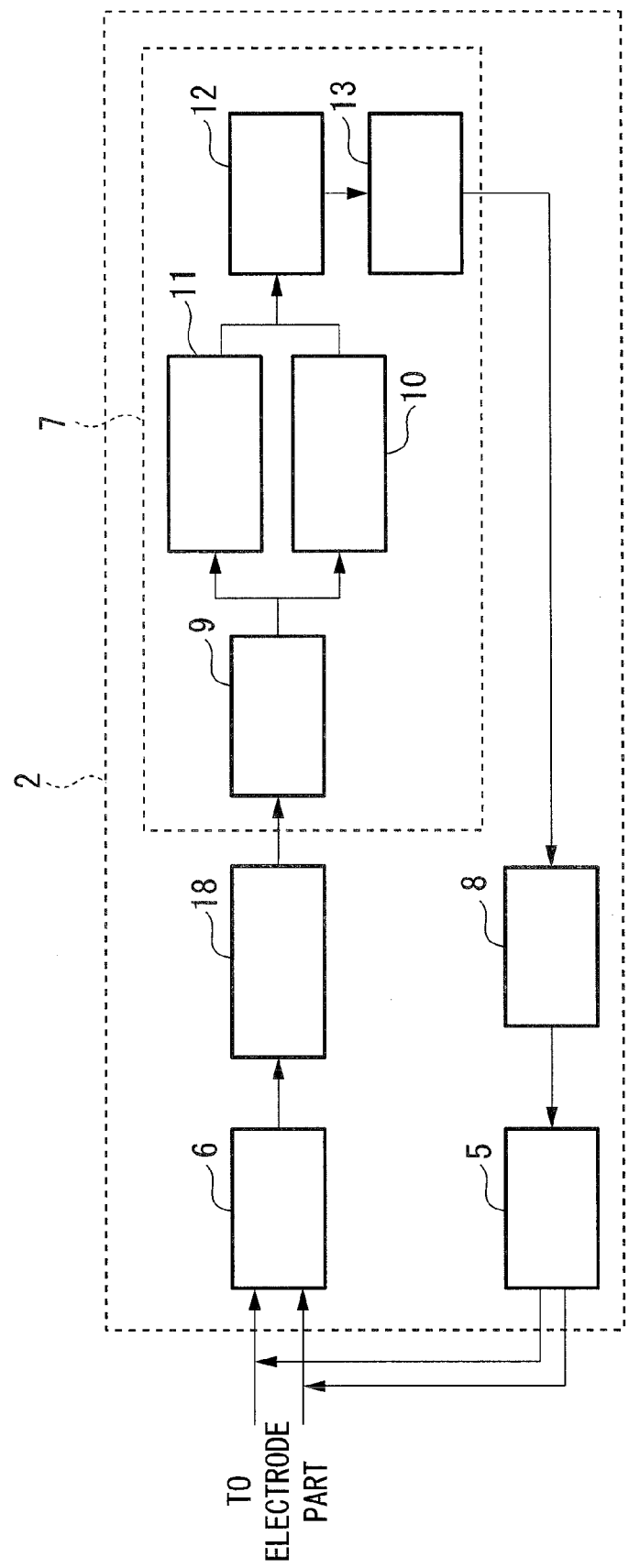
FIG. 7 is a block diagram of a still another modified example of the nerve stimulation device in FIG. 1, showing functions when a filtering part is provided.

In the above embodiment, a filtering part that removes a noise from the electric signal detected by the electrode part 4 may be provided. As the filtering part, for example, as shown in FIG. 7, a filter circuit (filtering part) 18 is used that removes high-frequency components so that a peak of R wave of spontaneous cardiac beat, and a waveform having a voltage smaller than those of the shock pulse and the pacing pulse and varying finely are removed.

In this manner, it is possible to distinguish the electric signal resulting from the cardiac event from relatively weak electric signals transmitted from tissues other than the heart B, an electric signal resulting from physiological excitation of the vagus nerve A, and noises contained in the course of transmission through the lead 3 from the electrode part 4 to the device main body 2, and to realize more accurate detection.

In the above embodiment, the specification of nerve stimulation by the stimulation signal outputting part 5 is not limited to the form as described above, and may be appropriately modified depending on the condition of the heart B of the individual patient. For example, for a patient not always requiring suppression of increase in cardiac rate, fibrillation or tachycardia may be prevented from sequentially reoccurring by starting vagus nerve stimulation upon occurrence of fibrillation or tachycardia and continuing the vagus nerve stimulation intermittently for a certain period of time.

What is claimed is:

1. A nerve stimulation device which is individually implanted in a body with a cardiac treatment device supplying an electric pulse to a heart depending on a cardiac rate, the nerve stimulation device comprising:
    a stimulation signal outputting part that stimulates a vagus nerve via a stimulation electrode adapted to be located on the vagus nerve;

an electric signal detecting part that detects an electric signal transmitted through a tissue outside the heart by a detection electrode adapted to be located on the tissue;

a cardiac event determining part that determines a cardiac event containing the electric pulse supplied to the heart by the cardiac treatment device, based on the electric signal detected by the electric signal detecting part; and a controlling part that controls the stimulation signal outputting part based on the cardiac event determined by the cardiac event determining part, wherein the nerve stimulation device is configured to be electrically separated from the cardiac treatment device.

2. The nerve stimulation device according to claim 1, comprising a filtering part that removes a noise from the electric signal detected by the electric signal detecting part.

3. The nerve stimulation device according to claim 1, wherein the cardiac event determining part determines that the electric pulse is a shock pulse for defibrillation when a voltage of the electric signal detected by the electric signal detecting part is more than or equal to a predetermined threshold.

4. The nerve stimulation device according to claim 3, wherein the controlling part attenuates stimulation on the vagus nerve by the stimulation signal outputting part when the cardiac event determining part determines that the electric pulse is the shock pulse.

5. The nerve stimulation device according to claim 3, wherein the controlling part enhances stimulation on the vagus nerve by the stimulation signal outputting part when the cardiac event determining part determines that the electric pulse is the shock pulse.

6. The nerve stimulation device according to claim 1, wherein the cardiac event determining part determines that the electric pulse is a pacing pulse for pacing a cardiac beat, when a voltage of the electric signal detected by the electric signal detecting part is more than or equal to a first predetermined threshold, and is smaller than a second predetermined threshold that is larger than the first predetermined threshold.

7. The nerve stimulation device according to claim 6, wherein the cardiac event determining part determines that the pacing pulse is an antitachycardia pacing pulse when it sequentially determines that the electric pulse is the pacing pulse in a time interval shorter than a predetermined time, and the number of sequential determinations of the pacing pulse is more than or equal to a predetermined threshold.

8. The nerve stimulation device according to claim 7, wherein the controlling part enhances stimulation on the vagus nerve by the stimulation signal outputting part when the cardiac event determining part determines that the electric pulse is the antitachycardia pacing pulse.

9. The nerve stimulation device according to claim 6, wherein the cardiac event determining part determines that the pacing pulse is a bradycardia pacing pulse when it sequentially determines that the electric pulse is a pacing pulse in a time interval shorter than a predetermined time, and the number of sequential determinations of the pacing pulse is smaller than a predetermined threshold.

10. The nerve stimulation device according to claim 9, wherein the controlling part attenuates stimulation on the vagus nerve by the stimulation signal outputting part when the cardiac event determining part determines that the electric pulse is the bradycardia pacing pulse.

* * * * *